United States Patent [19]

Seipp et al.

[11] Patent Number: 5,326,902

[45] Date of Patent: Jul. 5, 1994

[54] OXYALKYNE COMPOUNDS, PHARMACEUTICAL COMPOSITIONS CONTAINING THEM AND PROCESSES FOR PREPARING SUCH COMPOUNDS AND COMPOSITIONS

[75] Inventors: Ulrich Seipp, Aachen; Werner Vollenberg; Werner Englberger, both of Stolberg; Cornelia Geist, Aachen; Michael Haurand, Stolberg, all of Fed. Rep. of Germany

[73] Assignee: Gruenenthal GmbH, Aachen, Fed. Rep. of Germany

[21] Appl. No.: 36,331

[22] Filed: Mar. 24, 1993

[30] Foreign Application Priority Data

Mar. 30, 1992 [DE] Fed. Rep. of Germany ....... 4210332

[51] Int. Cl.$^5$ ...................... C07C 67/00; A61K 31/38; C07D 307/52
[52] U.S. Cl. .................................. 560/254; 560/221; 560/223; 560/225; 560/250; 560/251; 560/255; 549/29; 549/74; 549/75; 549/76; 549/77; 546/339; 546/340; 546/346; 574/438; 574/311; 574/337; 574/443
[58] Field of Search ............... 560/250, 251, 254, 255, 560/147, 152, 205, 221, 223, 225; 549/1, 29, 74, 75, 76, 77; 546/339, 340, 346

[56] References Cited

U.S. PATENT DOCUMENTS

| | | | |
|---|---|---|---|
| 4,652,584 | 3/1987 | Carson | 560/250 X |
| 4,937,373 | 6/1990 | Carson et al. | 560/53 X |
| 4,985,442 | 1/1991 | Batt | 560/62 X |
| 5,202,349 | 4/1993 | Zimmer et al. | 514/438 |

FOREIGN PATENT DOCUMENTS

| | | |
|---|---|---|
| 0279281 | 8/1988 | European Pat. Off. |
| 0292699 | 11/1988 | European Pat. Off. |
| 0452908 | 10/1991 | European Pat. Off. |
| 0468281 | 1/1992 | European Pat. Off. |

OTHER PUBLICATIONS

Journal of the American Chemical Society: vol. 87, pp. 5661–5670 (1965).
Journal of the American Chemical Society: vol. 89, pp. 5505–5507 (1965).
Corey et al., "Pyriddium Chlorochromate, An Efficient Reagent for Oxidation of Primary and Secondary Alcohols to Carbonyl Compounds", *Tetrahedron Lett.*, No. 31, pp. 2647–2650 (1975).
Mancuso et al., "Oxidation of Long-Chaain and Related Alcohols to Carbonyls bby Dimethyl Sulfoxide 'Activated' by Oxalyl Chloride", *J. Organic Chem.*, vol. 43, No. 12, pp. 2480–2482 (1978).
Summers et al., "Orally Active Hydroxamic Acid Inhibitors of Leukotriene Biosynthesis", *J. Med. Chem.*, vol. 31, pp. 3–5 (1988).
Tateson et al., "Selective Inhibition of Arachidonate 5-Lipoxygenase by Novel Acetohydroxamic Acids: Biochemical Assessment in vitro and ex vivo", *Brit. J. Pharacol.*, vol. 94, pp. 528–539 (1988).
Pratt et al., "Oxidation by Solids. I. Oxidation of Selected Alcohols by Manganese Dioxide", *J. Organic. Chem.*, vol. 26, pp. 2973–2975 (1961).
Corey et al., "Useful Procedures for the Oxidation of Alcohols Involving Pyridinium Dichromate in Aprotic Media", *Tetrahedron Lett.*, No. 5, pp. 399–402 (1979).

*Primary Examiner*—Arthur C. Prescott
*Attorney, Agent, or Firm*—Evenson, McKeown, Edwards & Lenahan

[57] ABSTRACT

Oxyalkyne compounds corresponding to the formula I

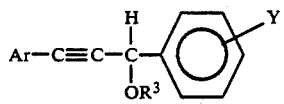

in which the substituent Y in the meta- or para-position is

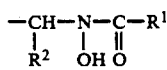

(Abstract continued at next page.)

$R^1$ represents $CH_3$ or $NH_2$, $R^2$ represents H or $CH_3$, $R^3$ represents H, $C_{1-3}$-alkyl or $COCH_3$, and Ar represents an aromatic residue selected from the group

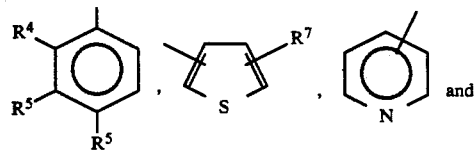

-continued

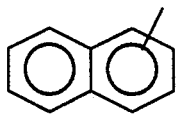

with the proviso that the substituents $R^4$, $R^5$ and $R^6$ are the same or different and each substituent represents H, F, Cl, Br, $C_{1-6}$-alkyl, $CF_3$ or $C_{1-6}$-alkoxy, and $R^7$ represents H, F, Cl, Br, $C_{1-3}$-alkyl or $CF_3$, in the form of their racemates or mixtures of diastereoisomers or in optically active form, which are suitable active ingredients in pharmaceutical compositions.

20 Claims, No Drawings

OXYALKYNE COMPOUNDS, PHARMACEUTICAL COMPOSITIONS CONTAINING THEM AND PROCESSES FOR PREPARING SUCH COMPOUNDS AND COMPOSITIONS

BACKGROUND OF THE INVENTION

This invention relates to oxyalkyne compounds corresponding to the formula I

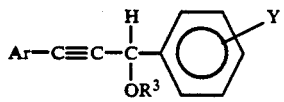

to pharmaceutical compositions containing at least one such oxyalkyne compound, as well as to processes for preparing such oxyalkyne compounds and pharmaceutical compositions.

Polyunsaturated higher fatty acids such as arachidonic acid serve in the metabolism of mammals, including humans, as substrates for the formation of physiologically and pathophysiologically important eicosanoids such as prostaglandins and leukotrienes. The pathway to prostaglandins is initiated by cyclooxygenase, whereas the pathway to leukotrienes is initiated by 5-lipoxygenase.

The prostaglandins are products having known beneficial functions in mammals, while it is known for the leukotrienes that they cause allergic reactions ranging up to anaphylactic and septic shock, bronchoconstriction, and asthma. Due to the numerous harmful effects of leukotrienes, there is a need for chemically and metabolically stable compounds which in the living organism have no effect on the biosynthesis of prostaglandins but selectively inhibit the activity of 5-lipoxygenase and thus prevent the formation of the undesired leukotrienes. Acetohydroxamic acid compounds which significantly inhibit the activity of 5-lipoxygenase but have no inhibitory action on cyclooxygenase are disclosed in Brit. J. Pharmacol. 94, 528 (1988). There remains a need, however, for other compounds exhibiting selective 5-lipoxygenase inhibiting activity.

SUMMARY OF THE INVENTION

It is the object of the invention to provide new compounds which selectively inhibit 5-lipoxygenase.

It is also an object of the invention to provide pharmacologically active compounds and pharmaceutical treatment methods which can be used to treat allergic reactions such as asthma.

These and other objects of the invention are achieved by providing an oxyalkyne compound corresponding to the formula I

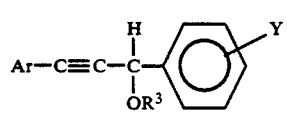

in which the substituent Y in the meta- or para-position is

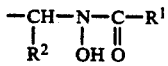

$R^1$ represents $CH_3$ or $NH_2$; $R^2$ represents H or $CH_3$; $R^3$ represents H, $C_{1-3}$-alkyl or $COCH_3$, and Ar represents an aromatic residue selected from the group consisting of

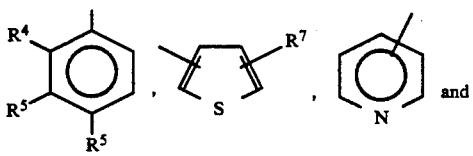

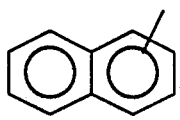

in which $R^4$, $R^5$ and $R^6$ are each independently selected from the group consisting of H, F, Cl, Br, $C_{1-6}$-alkyl, $CF_3$ and $C_{1-6}$-alkoxy, and $R^7$ represents H, F, Cl, Br, $C_{1-3}$-alkyl or $CF_3$, in the form of racemates or mixtures of diastereoisomers or in optically active form.

The objects of the invention are also achieved by providing a method of treating a patient suffering from a disorder attributable to the action of leukotrienes, comprising administering to the patient an effective 5-lipoxygenase inhibiting amount of at least one oxyalkyne compound as described above.

DETAILED DESCRIPTION OF PREFERRED EMBODIMENTS

It now has been found that certain, harmless oxyalkynes which are chemically and, when used as therapeutics, metabolically stable compounds, show a specific inhibiting effect on 5-lipoxygenase or 5- and 12-lipoxygenase but have no inhibitory action on cyclooxygenase.

Accordingly the present invention relates to oxyalkynes of formula I

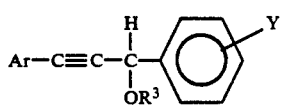

wherein the substituent Y in the meta- or para-position is

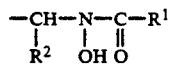

$R^1$ represents $CH_3$ or $NH_2$, $R^2$ represents H or $CH_3$, $R^3$ represents H, $C_{1-3}$-alkyl or $COCH_3$, and Ar represents an aromatic residue selected from the group consisting of

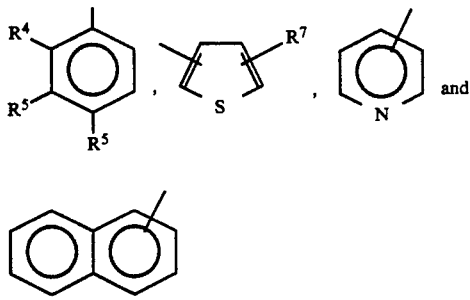

with the proviso that the substituents $R^4$, $R^5$ and $R^6$ are the same or different and each substituent represents H, F, Cl, Br, $C_{1-6}$-alkyl, $CF_3$ or $C_{1-6}$-alkoxy, and $R^7$ represents H, F, Cl, Br, $C_{1-3}$-alkyl or $CF_3$, in the form of their racemates or mixtures of diastereoisomers or in optically active form.

If the aromatic residue Ar is the pyridyl residue, the corresponding oxyalkyne contains either the 2-pyridyl, the 3-pyridyl or the 4-pyridyl residue. If the aromatic residue is the naphthyl residue, the corresponding oxyalkyne contains either the 1-naphthyl or the 2-naphthyl residue.

Compounds of formula I in which $R^2$ is H, and especially compounds of formula I in which $R^3$ is H, are preferred. If Ar represents the phenyl residue the substituents $R^4$, $R^5$ and $R^6$ may be the same or different. Preferably these substituents represent H, F, Cl or $OCH_3$. Preferred oxyalkynes in which Ar represents the phenyl residue are those in which at least one of the substituents $R^4$, $R^5$ and $R^6$ is H. Oxyalkynes in which Ar represents an unsubstituted phenyl residue or the 4-fluorophenyl residue are especially preferred. If Ar is the 2-thienyl or the 3-thienyl residue, $R^7$ preferably represents H. N-Hydroxy-N-[4-[1-hydroxy-3-phenyl-prop-2-yn-1-yl]benzyl ]acetamide and N-hydroxy-N-[4-[1-hydroxy-3-(4-fluorophenyl)prop-2-yn-1-yl]benzyl-]urea are examples of particularly suitable compounds.

The oxyalkynes of the invention selectively inhibit the activity of 5-lipoxygenase or of 5- and 12-lipoxygenase, but at the same concentration they have no effect on the activity of cyclooxygenase. Due to their selective inhibitory action on 5-lipoxygenase or 5- and 12-lipoxygenase, and thus on production of metabolites of arachidonic acid such as 5-hydroxyeicosatetraenoic acid (5-HETE), 12-HETE, 5S,12S-DiHETE, $LTB_4$, $LTC_4$, $LTD_4$ and $LTE_4$, the compounds according to the invention exhibit various physiologically valuable properties such as anti-anaphylactic, anti-asthmatic, anti-allergic, anti-phlogistic, blood pressure lowering, cerebral- and coronary-circulation improving as well as anti-psoriatic effects. Further the compounds according to the invention decrease the risk of leucocyte aggregation and the formation of leucocyte thrombi. Due to their chemical stability, and to their metabolic stability when used as therapeutic agents, the oxyalkynes of formula I are useful as medicaments such as anti-allergic, anti-anaphylactic, anti-phlogistic, anti-asthmatic, anti-hypertensive and anti-thrombotic agents, as agents for use in treatment or prophylaxis of ischemic myocardial infarction, as agents for use in treatment of disorders of coronary and/or cerebral vessels, or as agents for inhibiting the formation of metastasis.

The oxyalkynes of formula I have a low degree of toxicity. Accordingly, these compounds may be administered to humans and animals in the form of suitable pharmaceutical compositions.

The invention also relates to pharmaceutical compositions or medicaments containing as active ingredient at least one oxyalkyne of formula I. The dosage of the active ingredient to be administered to a patient depends on the body weight, on the form and route of administration, on the indication, and on the state of disease in the patient to be treated. In consideration of these factors, a unit dose form of a medicament according to the invention generally will contain from about 0.01 to 1000 mg of the active ingredient. Compositions for oral administration generally will preferably contain from about 1 to 1000 mg of active ingredient per unit dose. Compositions for parenteral administration generally will preferably contain from about 0.1 to 1000 mg of active substance per unit dose. Compositions for topical or inhalative administration generally will preferably contain from about 0.01 to 100 mg of the active ingredient per unit dose.

Compositions for oral administration, such as tablets, dragees, capsules, granules, drops or syrups, are very suitable for prophylactic or therapeutic administration of the compounds of formula I. The compounds of formula I may also be administered in the form of suppositories or compositions for percutaneous administration, such as a plaster or a solution containing the active ingredient, optionally with the addition of a known skin penetration enhancing agent. Advantageously these orally, rectally or percutaneously administrable forms are produced in such a way that the active ingredient is released therefrom in a delayed fashion in order to assure a uniform supply of the active ingredient to the patient over an extended period of time, for example 24 hours.

The medicaments for parenteral administration may be solutions, suspensions or dry formulations suitable for easy reconstitution. Spray forms are very useful application forms for intranasal or inhalative administration.

All of the general types of pharmaceutical compositions to which the invention is applicable as well as the preparation of these compositions are known in the art. Since the compounds of formula I are chemically stable, their incorporation into these pharmaceutical compositions in the form and dosage desired poses no problems for an ordinarily skilled pharmacist. In the production of pharmaceutical compositions according to the invention the usual care must naturally be taken in the selection of inorganic or organic adjuvants such as carriers, diluents, solvents, binders, tablet disintegrating agents, coloring agents, flavorings, and in particular in the production of compositions for parenteral administration care should be taken to achieve sterility and, if the compositions are in liquid form, isotonicity.

The invention also relates to a process for preparing an oxyalkyne compound corresponding to the formula I

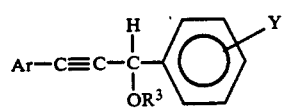

wherein the substituent Y in the meta- or para-position is

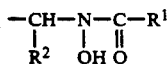

$R^1$ represents $CH_3$ or $NH_2$, $R^2$ represents H or $CH_3$, $R^3$ represents H, $C_{1-3}$-alkyl or $COCH_3$, and Ar represents an aromatic residue selected from the group consisting of

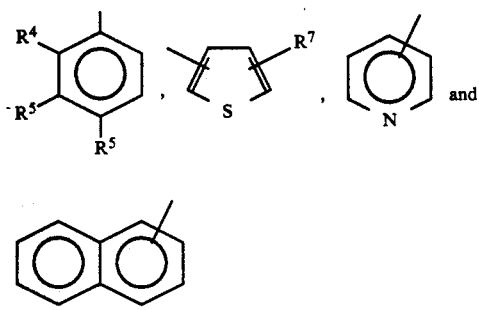

with the proviso that the substituents $R^4$, $R^5$ and $R^6$ may be the same or different and each substituent represents H, F, Cl, Br, $C_{1-6}$-alkyl, $CF_3$ or $C_{1-6}$-alkoxy, and $R^7$ represents H, F, Cl, Br, $C_{1-3}$-alkyl or $CF_3$, said process comprising
reacting an alkyne of formula II

with a partially protected terephthal or isophthal aldehyde of formula III

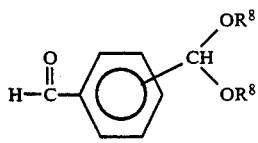

wherein $R^8$ represents $CH_3$ or $CH_2CH_3$, or both $R^8$ residues together represent the ethylene group, in the presence of a base to form an acetal of formula IV

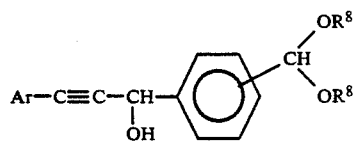

reacting the resulting acetal with an acid in a water containing solvent to form a hydroxy aldehyde of formula V

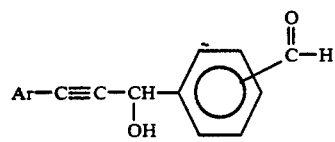

transforming the resulting hydroxy aldehyde into an oxime of formula VI

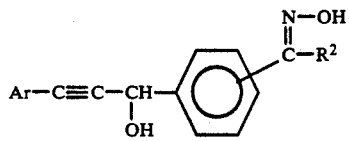

by either
reacting a hydroxy aldehyde of formula V with hydroxyl amine or a salt thereof in the presence of a base, or substituting the alcoholic proton of the hydroxy aldehyde of formula V with an acid cleavable group which does not react with a Grignard reagent, then reacting with a methyl magnesium halogenide in an anhydrous nucleophilic solvent, oxidizing the resulting secondary alcohol with an oxidizing agent and transforming the resulting keto compound by splitting off the acid cleavable group with an acid into a keto compound of formula Va

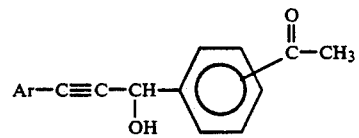

from which an oxime of formula VI is prepared by reaction with a hydroxylamine or a salt thereof in the presence of a base, reducing the resulting oxime with a boron-containing reducing agent in the presence of an acid, and optionally a $C_{1-3}$-alkyl alcohol, to a hydroxylamine of formula VII

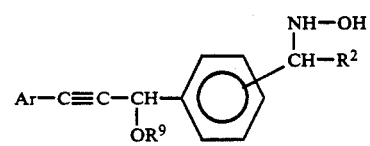

wherein $R^9$ represents H or $C_{1-3}$-alkyl, and then transforming the resulting hydroxylamine into an oxyalkyne of formula I by a) reaction with trimethylsilyl isocyanate or an alkali cyanate followed by hydrolysis or with phosgene followed by aminolysis, or b) reaction with an acetylating agent followed by treatment with a base to split off the O-acetyl group of the resulting his-acetyl compound, and optionally transforming the propargylic $OCOCH_3$-group into the OH-group. Acetals of formula IV are prepared in a known manner by reacting an alkyne of formula II at $-75°$ C. to $25°$ C. with a strong base, e.g. n-butyl lithium or a Grignard reagent, in an anhydrous solvent or solvent mixture such as tetrahydrofuran, diethyl ether, ethylene- and/or diethylene glycol dimethyl ether, and then with 1 to 1.1 mole (based on the amount of alkyne) of a partially protected terephthal aldehyde or isophthal aldehyde such as terephthal aldehyde monodimethylacetal or -monodiethylacetal or isophthal aldehyde monodimethylacetal or -monodiethylacetal. By reacting the resulting acetal with an acid, for example hydrochloric acid, or the pyridinium salt of p-toluenesulfonic acid, at $0°$ C. to $50°$ C. in a water-containing solvent or solvent mixture such as methanol, ethanol and/or tetrahydrofuran, a hydroxy aldehyde of formula V is obtained.

To prepare an oxyalkyne of formula I in which $R^2$ is $CH_3$, the alcoholic proton of a hydroxy aldehyde of formula V is first substituted with an acid clearable group which does not react with a Grignard reagent, for example the tetrahydropyranyl, tert.-butyldiphenylsilyl, tert.butyldimethylsilyl, isopropyldimethylsilyl, triethylsilyl or trimethylsilyl group. Then the resulting aldehyde is reacted with methylmagnesium iodide, bromide or chloride in an anhydrous nucleophilic solvent or solvent mixture containing no active hydrogen, for example tetrahydrofuran, ethylene glycol dimethyl ether and/or diethyl ether at a temperature between 0° C. and 50° C. to form the corresponding secondary alcohol. By oxidizing the resulting secondary alcohol with $SO_3$-pyridine complex in dimethyl sulfoxide (*J. Am. Chem. Soc.* 89, 5505 (1967)), manganese dioxide (*J. Org. Chem.* 26, 2973 (1961)), pyridinium dichromate (*Tetrahedron Lett.* 1979, 399), pyridinium chlorochromate (*Tetrahedron Lett.* 1975, 2647), dicyclohexyl carbodiimide/dimethyl sulfoxide/pyridinium trifluoroacetate (*J. Am. Chem. Soc.* 87, 5661 (1965)) or oxalyl chloride/dimethyl sulfoxide (*J. Org. Chem.* 43, 2480 (1978)) and then splitting off the acid cleavable group with an acid, for example hydrochloric acid, or the pyridinium salt of p-toluenesulfonic acid in a water-containing, alcohol-free solvent or solvent mixture, such as tetrahydrofuran, diethyl ether and/or ethyl acetate, at 20° C. to 70° C., a keto compound of formula Va

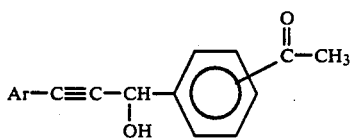

is formed. The resulting keto compound may be transformed into an oxime of formula VI by reaction with 1.2 to 2 moles of hydroxylamine and/or a salt thereof, for example hydroxylamine hydrochloride, in a polar solvent or solvent mixture, such as methanol, ethanol, tetrahydrofuran or aqueous mixtures of these solvents, in the presence of a base, for example pyridine, sodium acetate, potassium or sodium carbonate at 15° C. to 60° C.

To prepare the preferred oxyalkynes of formula I, in which $R^2$ is H, a hydroxy aldehyde of formula V is converted with hydroxylamine and/or a salt thereof under the above mentioned conditions into an oxime of formula VI.

The oximes of formula VI are reduced by means of a boron hydride or a borane-amine-complex, e.g. sodium cyanoborohydride in acetic acid or methanolic, ethanolic, propanolic and/or isopropanolic hydrochloric acid at temperatures between 20° C. and 60° C. or borane-pyridinecomplex in at least one solvent such as tetrahydrofuran, methanol and/or ethanol, in the presence of hydrochloric acid at temperatures between 0° C. and 20° C. (J. B. Summers et al., *J. Med. Chem.* 31, 1960 (1988)). During the reduction in the acidic alcoholic medium, the propargylic hydroxy group is transformed into an ether group. The reduction is preferably carried out in the absence of a $C_{1-3}$-alkyl alcohol.

To prepare an oxyalkyne of formula I in which $R^1$ is $NH_2$, a hydroxylamine of formula VII may be reacted, after isolation from the reaction mixture in which it was prepared, with 1.1 to 2 moles of trimethylsilyl isocyanate in an inert solvent or solvent mixture, such as cyclic ethers, for example tetrahydrofuran and/or 1,4-dioxane at temperatures between 20° C. and the boiling temperature of the solvent used. Then the resulting intermediate is hydrolyzed with, for example, a saturated aqueous solution of ammonium or sodium chloride. Alternatively a compound according to the invention may be obtained by reacting a hydroxylamine of formula VII, optionally without isolation from the reaction mixture in which it was prepared, with potassium or sodium cyanate in acidic solution. Further an oxyalkyne of formula I may be prepared by reacting a hydroxylamine of formula VII, optionally without isolation from the reaction mixture in which it was prepared, with phosgene in the presence of an acid binding agent, for example sodium or potassium carbonate, followed by treatment with ammonia or an ammonia releasing compound, for example ammonium carbonate.

To prepare an oxyalkyne of formula I in which $R^1$ is CH3, a hydroxylamine of formula VII, optionally without isolation from the reaction mixture in which it was prepared, is reacted with 2.2 to 10 moles of an acetylating agent, preferably acetic anhydride, acetyl chloride or ethyl acetate, optionally in the presence of a base, e.g. pyridine or triethylamine, and in the presence of a solvent, for example toluene, to obtain the corresponding bis-acetyl compound. The O-acetyl group is split off from the bis-acetyl compound by treatment with a base, optionally in the presence of an alcohol, and optionally the propargylic $OCOCH_3$-group is converted into an OH-group in the presence of a solvent or solvent mixture such as methanol, ethanol or tetrahydrofuran at temperatures between 20° C. and 60° C. Suitable bases include lithium, sodium or potassium hydroxide, sodium or potassium carbonate, or sodium bicarbonate which optionally may be added in the form of an aqueous solution (J. B. Summers et al., *J. Med. Chem.* 31, 1960 (1988)).

Oxyalkynes of formula I in the form of their racemates or mixtures of diastereomers may be separated into the corresponding enantiomers or diastereomers by chromatography, optionally in the presence of a compound with an asymmetric center.

EXAMPLE 2

In the following examples, all temperature references are uncorrected. The $^1$H-nuclear magnetic spectra ($^1$H-NMR) were measured at 300MHz in DMSO-$d_6$. The chemical shifts are given in ppm. Column chromatography was carried out using silica gel ("Kieselgel 60", 0.040 to 0.063 mm from E. Merck of Darmstadt, Germany) as the stationary phase. The mixing ratios of the components of the solvent mixtures used either during a reaction or for chromatographic analysis are always given as volume/volume.

EXAMPLE 3

N-Hydroxy-N-[4-[1-hydroxy-3-phenyl-prop-2-yn-1-yl]benzyl]acetamide 178.8 ml of n-butyllithium (1.6 N solution in n-hexane) were introduced dropwise at −70° C. under an atmosphere of dry nitrogen to 31.6 ml of phenylacetylene in 600 ml of anhydrous tetrahydrofuran. After stirring at −70° C. for one hour, 57.4 ml of terephthal aldehyde monodiethylacetal in 600 ml of anhydrous tetrahydrofuran were added at −70° C. After stirring at −70° C. for another hour, the mixture was added to 500 ml of a saturated solution of sodium chloride and shaken with ethyl acetate. After drying over magnesium sulfate and separating the drying agent, ethyl acetate was evaporated at 40° C. and $2.7 \times 10^3$ Pa to yield 89 g of 1-(4-diethoxymethyl-phenyl)-3-phenyl-prop-2-yn-1-ol in the form of a yellow oil.

To 185 g of 1-(4-diethoxymethylphenyl)-3-phenyl-prop-2-yn-1-ol in 1.8 liters of a 9:1 mixture of tetrahydrofuran and water were added 30 g of p-toluenesulfonic acid pyridinium salt. After stirring at 20° C. for 15 hours, 500 ml of a saturated aqueous solution of sodium bicarbonate were added. The organic layer was separated, and after drying over magnesium sulfate, the drying agent was separated, and ethyl acetate was distilled off at 40° C. and $2.7 \times 10^3$ Pa to yield 131 g of 1-(4-formylphenyl)-3-phenylprop-2-yn-1-ol in the form of a yellow oil. The resulting oil was stirred together with 57.9 g of hydroxylamine hydrochloride and 44 g of sodium carbonate in 1.1 liters of tetrahydrofuran/water 4:1 at 20° C. for 15 hours. Then 500 ml of a saturated aqueous solution of sodium chloride were added. The reaction mixture was shaken with ethyl acetate. After drying the organic layer over magnesium sulfate, the drying agent was separated by filtration at 40° C. and $2.7 \times 10^3$ Pa to yield 153 g of the oxime 1-(4-hydroxyiminomethylphenyl)-3-phenyl-prop-2-yn-1-ol, syn/anti-mixture, in the form of a colorless solid.

10 g of the resulting oxime were dissolved in 140 ml of tetrahydrofuran. After adding 8 ml of borane-pyridine complex at 0° C., the mixture was stirred for 15 minutes. Then 20 ml of concentrated hydrochloric acid were added at 0° C. After stirring at 0° C. for one hour, 100 ml of water and 12.8 g of sodium carbonate were added to the mixture, resulting in a pH-value of the, aqueous layer of 8.5. After separating the organic layer, the aqueous layer was washed with ethyl acetate. After drying the organic extracts over magnesium sulfate and separating the drying agent, the solvent was distilled off at 40° C. and $2.7 \times 10^3$ Pa to yield 10.6 g of 1-(4-hydroxyaminomethylphenyl)-3-phenyl-prop-2-yn-1-ol in the form of a yellow oil.

To a solution of 118 g of the hydroxylamine obtained as described above, dissolved in 850 ml of toluene, 250 ml of acetic anhydride and 200 ml of pyridine were added dropwise at 5° C. After stirring at 5° C. for 15 minutes and at 20° C. for 15 hours, the reaction mixture was added to 150 ml of concentrated hydrochloric acid in 3 liters of water while cooling. After separating the organic layer, the aqueous layer was shaken with 500 ml of ethyl acetate and washed with 250 ml of a saturated aqueous solution of sodium chloride. After drying the organic layer over magnesium sulfate and separating the drying agent, the solvent was evaporated at 40° C. and $2.7 \times 10^3$ Pa to yield 157 g of N-acetoxy-N-[4-[1-acetoxy-3-phenyl-prop-2-yn-1-yl]benzyl]-acetamide in the form of a yellow oil.

To 140 g of the resulting acetylated acetamide dissolved in 1 liter of tetrahydrofuran, 1 liter of a 2 N methanolic solution of lithium hydroxide was added at 20° C. After stirring for 15 hours, the reaction mixture was added to 1 liter of water, and the pH-value was adjusted to 5.5 by addition of 500 ml of 10% by weight of hydrochloric acid. After separating the organic layer, the aqueous layer was shaken with ethyl acetate, washed with a saturated aqueous solution of sodium chloride, and then the organic layers were dried over magnesium sulfate. After separating the drying agent, the solvent was evaporated at 40° C. and $2.7 \times 10^3$ Pa to yield 120 g of an oily residue which was dissolved in 1 liter of ethyl acetate. To this solution 1 liter of hexane was added. After stirring for 30 minutes and filtering, 1 liter of hexane was added to the filtrate to yield 56 g of racemic N-hydroxy-N-[4-[1-hydroxy-3-phenylprop-2-yn-1-yl]benzyl]acetamide in the form of colorless crystals melting at 121° C. to 123° C.

$^1$H-NMR: 2.04 (s, 3H); 4.76 (s, 2H); 5.31 (s, 1H); 5.63 (d, 3Hz, 1H); 7.30–7.44 (m, 7H); 7.57 (d, 8Hz, 2H); 9.43 (s, 1H).

EXAMPLE 2:

(+)-N-Hydroxy-N-[4-[1-hydroxy-3-phenyl-prop-2-yn-1-yl]benzyl]acetamide.

The racemic N-hydroxy-N-[4-[1-hydroxy-3-phenyl-prop-2-yn-1-yl]benzyl]acetamide prepared according to Example 1 was chromatographed with methanol/water 90:10 using tribenzoyl cellulose (10 to 20 μm from Riedl de Haen, Germany) as the stationary phase.

$[\alpha]^{21}_D$: +1.80° (c=0,06 Mole/liter methanol)
Melting point: 112° to 115° C.

EXAMPLE '

(−)-N-Hydroxy-N-[4-[1-hydroxy-3-phenyl-prop-2-yn-1-yl]benzyl]acetamide

The racemic N-hydroxy-N-[4-[1-hydroxy-3-phenyl-prop-2-yn-1-yl]benzyl]acetamide prepared according to Example 1 was chromatographed according to Example 2.

$[\alpha]^{21}_D$: −1.90° (c=0,05 Mole/liter methanol)
Melting point: 117° to 119° C.

EXAMPLE 4

N-Hydroxy-N-[4-[1-acetoxy-3-phenyl-prop-2-yn-1-yl]benzyl]acetamide 38 g of N-acetoxy-N-[4-[1-acetoxy-3-phenyl-prop-2-yn-1-yl]benzyl]acetamide prepared according to Example 1 were dissolved in a mixture of 180 ml of methanol and 20 ml of water. After adding 0.84 g of sodium bicarbonate the reaction mixture was stirred at 20° C. for 7 hours. Then the mixture was added to 500 ml of a saturated aqueous solution of sodium chloride and shaken with ethyl acetate. The organic layer was washed with a saturated aqueous solution of sodium chloride and dried over magnesium sulfate. After separating the drying agent by filtration, the solvent was evaporated at 40° C. and $2.7 \times 10^3$ Pa to yield 3.3 g of a residue which was chromatographed with toluene/methanol/ acetic acid 4.7:0.3:0.025. 2.9 g of N-hydroxy-N-[4-[1-acetoxy-3-phenyl-prop-2-yn-1-yl]benzyl]acetamide were obtained in the form of a yellow oil.

$^1$H-NMR: 2.07 (s, 3H); 2.10 (s, 3H); 4.72 (s, 2H); 6.64 (s, 1H); 7.34–7.58 (m, 9H); 9.90 (s, 1H)

EXAMPLE 5

N-Hydroxy-N-[4-[1-ethoxy-2-phenyl-prop-2-yn-1-yl]benzyl]acetamide.

To 5 g of 1-(4-hydroxyiminomethylphenyl)-3-phenyl-prop-2-yn-1-ol syn/anti-mixture prepared according to Example 1 and dissolved in 120 ml of ethanol were added 8 ml of borane-pyridine complex at 0° C. and then 12 ml of an ethanolic 20% by weight solution of hydrochloric acid. After stirring at 0° C. for one hour and at 20° C. for 2 hours, the reaction mixture was added to 1.2 liters of a saturated aqueous solution of sodium bicarbonate and shaken with ethyl acetate. The organic layer was dried over magnesium sulfate. After filtration and evaporation of the solvent at 40° C. and $2.7 \times 10^3$ Pa, the resulting residue (8.1 g) was chromatographed with methylene chloride/methanol 4.7:0.3 to yield 2.3 g of 1-(4-hydroxyaminomethylphenyl)-3-phenyl-1-ethoxy-prop-2-yne in the form of a colorless oil. Following the procedure of Example 1, the resulting oil was converted into N-acetoxy-N-[4-[1-ethoxy-3-phenyl-prop-2-yn-1-yl]-benzyl]acetamide and then into the yellow oil of N-hydroxy-N-[4-[1-ethoxy-3-phenyl-prop-2-yn-1-yl]benzyl]acetamide.

$^1$H-NMR: 1.19 (t, 7Hz, 3H); 2.06 (s, 3H); 3.52–3.57 (m, 1H); 3.70–3.75 (m, 1H); 4.70 (s, 2H); 5.46 (s, 1H); 7.24–7.51 (m, 9H); 9.88 (s, 1H)

EXAMPLE 6

N-Hydroxy-N-[1-[4-(1-hydroxy-3-phenyl-prop-2-yn-1-yl)phenyl]ethyl]acetamide

To 10 g of 1-(4-formylphenyl)-3-phenyl-prop-2-yn-1-ol prepared according to Example 1 and dissolved in 200 ml of anhydrous tetrahydrofuran were added 8.7 ml of trimethylchlorosilane and 9.4 ml of triethylamine at 20° C. After stirring for 15 minutes, the reaction mixture was added to 100 ml of a saturated aqueous solution of sodium bicarbonate and 200 ml of a saturated aqueous solution of sodium chloride and then shaken with ethyl acetate. The resulting organic layer was washed with a saturated aqueous solution of sodium bicarbonate, dried over potassium carbonate, filtered, and the resulting filtrate evaporated at 40° C. and $2.7 \times 10^3$ Pa. The oily residue obtained was chromatographed with hexane/ethyl acetate 4.5:0.5 to yield 12 g of 1-(4-formylphenyl)-3-phenyl-prop-2-in-1-trimethylsilyl ether in the form of a yellow oil.

5.75 g of the resulting silyl ether dissolved in 20 ml of anhydrous diethyl ether were added dropwise to a solution of methyl magnesium iodide prepared from 450 mg of magnesium and 2.6 g of methyl iodide in 90 ml of anhydrous diethyl ether at 20° C. After stirring at 20° C. for 30 minutes, 100 ml of a saturated aqueous solution of sodium chloride and 10 ml of an aqueous 0.1 N solution of sodium hydroxide were added to the reaction mixture. The solution was filtered through 5 g of diatomaceous earth. The solid residue obtained was washed with diethyl ether, and after separating the organic layer, the aqueous layer was washed with diethyl ether. After drying the organic extracts over potassium carbonate and separating the drying agent by filtration, the solvent was evaporated at 40° C. and $2.7 \times 10^3$ Pa to yield an oily residue (5.53 g) which was chromatographed with hexane/ ethyl acetate 4:1. 2.48 g of 1-[4-[1-hydroxyethyl]phenyl]-3-phenyl-prop-2-yne-1-trimethylsilyl ether were obtained in the form of a yellow oil. The oil was diluted with 15.5 ml of dimethyl sulfoxide, and 13.2 ml of triethylamine and 3.72 g of sulfur trioxide/pyridine-complex were added at 20° C. After stirring at 20° C. for 45 minutes, 90 ml of 1 N hydrochloric acid and 90 ml of a saturated aqueous solution of sodium chloride were added to the reaction mixture while cooling. Then the mixture was stirred for 5 minutes and shaken with ethyl acetate. The organic layer was dried over magnesium sulfate, the drying agent separated by filtration, and the solvent evaporated at 40° C. and $2.7 \times 10^3$ Pa. 2.62 g of a yellow oil were obtained which were dissolved in 10 ml of ethyl acetate and after addition of 5 ml of 1 N hydrochloric acid stirred at 20° C. for 15 hours. Then the organic layer was separated, and the aqueous layer washed with ethyl acetate. The organic layers were dried over magnesium sulfate, and after separating the drying agent, the solvent was evaporated at 40° C. and $2.7 \times 10^3$ Pa. The oily residue (2.42 g) was chromatographed with hexane/ethyl acetate 3.5:1.5 to yield 550 mg of 1-[4-[1-oxoethyl]phenyl]3-phenyl-prop-2-yn-1-ol in the form of a yellow oil which was converted in accordance with Example 1 into the corresponding oxime, hydroxylamine, acetylated acetamide and N-hydroxy-N-[1-[4-(1-hydroxy-3-phenyl-prop-2-yn-1-yl)-phenyl]ethyl]acetamide, mixture of diastereomers.

$^1$H-NMR: 1.48 (d, 7Hz, 3H); 2.04 (s, 3H); 5.6 (s, 1H); 5.65–5.68 (m, 1H); 7.35–7.54 (m, 9H)

EXAMPLE 7

N-Hydroxy-N-[1-[4-(1-acetoxy-3-Phenyl-prop-2-yn-1-yl)phenyl]ethyl]acetamide

N-Acetoxy-N-[1-[4-(1-acetoxy-3-phenyl-prop-2-yn-1-yl)phenyl]ethyl]acetamide prepared according to Example 6 was transformed into N-hydroxy-N-[1-[4-(1-acetoxy-3-phenyl-prop-2-yn-1-yl) phenyl]ethyl]acetamide, mixture of diastereomers following the procedure described in Example 4.

$^1$H-NMR: 147 (d, 7Hz, 3H); 2.03 (s, 3H); 2.10 (s, 3H); 5.63–5.66 (m, 1H); 6.64 (s, 1H); 7.45–7.56 (m, 9H); 9.58 (s, 1H)

EXAMPLE 8

N-Hydroxy-N-[4-[1-hydroxy-3-phenyl-prop-2-yn-1-yl]benzyl]urea 11.4 g of 1-(4-hydroxyareinomethylphenyl)-3-phenyl-prop-2-yn-1-ol prepared according to Example 1 were dissolved in 200 ml of tetrahydrofuran. To this solution were added 7.5 ml of trimethylsilyl isocyanate. After heating under reflux for 1 hour, the reaction mixture was allowed to cool at 20° C. and was added to 1 liter of a saturated aqueous solution of sodium chloride. After shaking with ethyl acetate, the organic layers were dried over magnesium sulfate, filtered, and the solvent was evaporated at 40° C. and $2.7 \times 10^3$ Pa. The residue (10.4 g) was chromatographed with hexane/isopropanol/acetic acid 4:1:0.01 and then recrystallized from hexane/acetone to yield 1.5 g of N-hydroxy-N-[4-[1-hydroxy-3-phenyl-prop-2-yn-1-yl]benzyl]urea which decomposed at 145° to 146° C.

H-NMR: 4.56 (s, 2H); 5.59 (d, 6Hz, 1H); 6.14 ( d, 6Hz, 1H); 6.37 ( s, 2H); 7.30–7.5 (m, 9H); 9.39 (s, 1H)

EXAMPLE 9

N-Hydroxy-N-[4-[1-hydroxy-3-(2-chlorophenyl)prop-2-yn-1-yl]benzyl]acetamide

The acetamide compound was prepared according to Example 1 using 2-chlorophenylacetylene instead of phenylacetylene.

$^1$H-NMR: 2.05 (s, 3H); 4.69 (s, 2H); 5.65 (s, 1H); 6.23 ( s, 1H); 7.11–7.58 (re, 8H); 9.96 (S, 1H)

EXAMPLE 10

N-Hydroxy-N-[4-[1-hydroxy-3-(3-chlorophenyl) prop-2-yn-1-yl]benzyl]acetamide

The acetamide compound was prepared according to Example 1 using 3-chlorophenylacetylene instead of phenylacetylene.

$^1$H-NMR: 2.05 (s, 3H); 4.69 (s, 2H); 5.60 (d, 6Hz, 1H); 6.19 (d, 6Hz, 1H); 7.29 (d, 8Hz, 2H); 7.39–7.52 (m, 6H); 9.87 (s, 1H)

EXAMPLE 11

N-Hydroxy-N-[4-[1-hydroxy-3-(4-chlorophenyl)prop-2-yn-1-yl]benzyl]acetamide

The acetamide compound was prepared according to Example 1 using 4-chlorophenylacetylene instead of phenylacetylene.

$^1$H-NMR: 2.05 (s, 3H); 4.69 (s, 2H); 5.59 (d, 6Hz, 1H); 6.18 (d, 6Hz, 1H); 7.29 (d, 8Hz, 2H); 7.42 (d, 7Hz, 1H); 7.45 (d, 7Hz, 1H); 7.51 (d, 8Hz, 2H); 9.87 (s, 1H)

EXAMPLE 12

N-Hydroxy-N-[4-[1-hydroxy-3-(4-fluorophenyl)prop-2-yn-1-yn-1-yl]benzyl]acetamide The acetamide compound was prepared according to Example 1 using 4-fluorophenylacetylene instead of phenylacetylene.

$^1$H-NMR: 2.07 (s, 3H); 4.71 (s, 2H); 5.61 (d, 6Hz, 1H); 6.20 (d, 6Hz, 1H); 7.21 (t, 9Hz, 2H); 7.31 (d, 8Hz, 2H); 7.49–7.55 (m, 4H); 9.91 (s, 1H)

EXAMPLE 13

N-Hydroxy-N-[4-[1-hydroxy-3-(3-methoxyphenyl)prop-2-yn-1-yl]benzyl]acetamide

The acetamide compound was prepared according to Example 1 using 3-methoxyphenylacetylene instead of phenylacetylene.

$^1$H-NMR: 2.05 (s, 3H); 3.76 (s, 3H); 4.69 (s, 2H); 5.59 (d, 6Hz, 1H); 6.15 (d, 6Hz, 1H); 6.93–7.03 (m, 3H); 7.25–7.30 (m, 3H); 7.51 (d, 8Hz, 2H); 9.88 (s, 1H)

EXAMPLE 14

N-Hydroxy-N-[4-[1-hydroxy-3-(3,4-dimethoxyphenyl)prop-2-yn-1-yl]benzyl]acetamide The acetamide compound was prepared according to Example 1 using 3,4-dimethoxyphenylacetylene instead of phenylacetylene.

$^1$H-NMR: 2.05 (s, 3H); 3.76 (s, 3H); 3.78 (s, 3H); 4.68 (s, 2H); 5.56 (d, 6Hz, 1H); 6.08 (d, 6Hz, 1H); 6.90–7.02 (m, 3H); 7.27 (d, 8Hz, 2H); 7.50 (d, 8Hz, 2H); 9.87 (s, 1H)

EXAMPLE 15

N-Hydroxy-N-[4-[1-hydroxy-3-(1-naphthyl)prop-2-yn-1-yl]benzyl]acetamide

The acetamide compound was prepared according to Example 1 using 1-naphthylacetylene instead of phenylacetylene.

$^1$H-NMR: 2.06 (s, 3H); 4.72 (s, 2H); 5.77 (d, 6Hz, 1H); 6.31 (d, 6Hz, 1H); 7.33 (d, 8Hz, 2H); 7.50 (t, 8Hz, 1H); 7.55–7.71 (m, 5H); 7.94–7.98 (m, 2H); 8.27 (d, 8Hz, 1H); 9.89 (s, 1H)

EXAMPLE 16

N-Hydroxy-N-[4-[1-hydroxy-3-(2-thienyl)prop-2-yn-1-yl]benzyl]acetamide

The acetamide compound was prepared according to Example 1 using 2-thienylacetylene instead of phenylacetylene.

Melting point: 125° to 126° C.

$^1$H-NMR: 2.04 (s, 3H); 4.68 (s, 2H); 5.60 (d, 6Hz, 1H); 6.18 (d, 6Hz, 1H); 7.05 (t, 4Hz, 1H); 7.26–7.29 (m, 3H); 7.47 (d, 8Hz, 2H); 7.56 (d, 5Hz, 1H); 9.84 (s, 1H)

EXAMPLE 17

N-Hydroxy-N-[4-[1-hydroxy-3-(3-thienyl)prop-2-yn-1-yl]benzyl]acetamide

The acetamide compound was prepared according to Example 1 using 3-thienylacetylene instead of phenylacetylene.

Melting point: 126° to 129° C.

$^1$H-NMR: 2.05 (s, 3H); 4.68 (s, 2H); 5.56 (s, 1H); 6.13 (s, 1H); 7.15 (d, 5Hz, 1H); 7.28 (d, 8Hz, 2H); 7.49 (d, 8Hz, 2H); 7.50–7.58 (m, 1H); 7.74 (d, 2Hz, 1H); 9.89 (S, 1H)

EXAMPLE 18

N-Hydroxy-N-[4-[1-hydroxy-3-(3-pyridyl)prop-2-yn-1-yl]benzyl]acetamide

The acetamide compound was prepared according to Example 1 using 3-pyridylacetylene instead of phenylacetylene.

Melting point: 145° to 146° C.

$^1$H-NMR: 2.04 (s, 3H); 4.68 (s, 2H); 5.62 (d, 6Hz, 1H); 6.21 (d, 6Hz, 1H); 7.28 (d, 8Hz, 2H); 7.38–7.43 (m, 1H); 7.51 (d, 8Hz, 2H); 7.86 (dd, 2Hz, 1H); 8.55 (dd, 1Hz, 1H); 8.63 (s, 1H); 9.36 (s, 1H)

EXAMPLE 19

N-Hydroxy-N-[3-[1-hydroxy-3-phenyl-prop-2-yn-1-yl]benzyl]acetamide

The acetamide compound was prepared according to Example 1 using isophthal aldehyde monodiethylacetal instead of terephthal aldehyde monodiethylacetal.

Melting point: 104° C.

$^1$H-NMR: 2.05 (s, 3H); 4.71 (s, 2H); 5.59 (s, 1H); 6.17 (s, 1H); 7.20–7.22 (m, 1H); 7.32–7.46 (m, 8H); 9.91 (s, 1H)

EXAMPLE 20

N-Hydroxy-N-[3-[1-hydroxy-3-(3-thienyl)prop-2-yn-1-yl]benzyl]acetamide

The acetamide compound was prepared according to Example 1 using 3-thienylacetylene instead of phenylacetylene and isophthal aldehyde monodiethylacetal instead of terephthal aldehyde monodiethylacetal.

Melting point: 133° C.

$^1$H-NMR: 2.05 (s, 3H); 4.70 (s, 2H); 5.56 (s, 1H); 6.15 (s, 1H); 7.16 (m, 1H); 7.20 (d, 7Hz, 1H); 7.34 (t, 8Hz, 1H); 7.42–7.44 (m, 2H); 7.57–7.60 (m, 1H); 7.76 (d, 2Hz, 1H); 9.92 (s, 1H)

EXAMPLE 21

N-Hydroxy-N-[3-[1-hydroxy-3-(3,4-dimethoxyphenyl)-prop-2-yn-1-yl]benzyl]acetamide The acetamide compound was prepared according to Example 1 using 3,4-dimethoxyphenylacetylene instead of phenylacetylene and isophthal aldehyde monodiethylacetal instead of terephthal aldehyde monodiethylacetal.

$^1$H-NMR: 2.05 (s, 3H); 3.77 (s, 6H); 4.71 (s, 2H); 5.60 (s, 1H); 6.12 (s, 1H); 6.91–7.04 (m, 3H); 7.20–7.22 (m, 1H); 7.32–7.37 (m, 1H); 7.44–7.47 (m, 2H); 9.91 (S, 1H)

EXAMPLE 22

N-Hydroxy-N-[4-[1-hydroxy-3-(2-chlorophenyl)prop-2-yn-1-yl]benzyl]urea

Following the procedure described in Example 1 the corresponding hydroxylamine was prepared from 2-chlorophenylacetylene and converted into the urea compound according to Example 8.
Melting point: 134° to 136° C.
$^1$H-NMR: 4.56 (s, 2H); 5.65 (d, 6Hz, 1H); 6.22 (d, 6Hz, 1H); 6.38 (s, 2H); 7.31–7.42 (m, 4H); 7.52–7.58 (m, 4H); 9.38 (s, 1H)

EXAMPLE 23

N-Hydroxy-N-[4-[1-hydroxy-3-(3-chlorophenyl)prop-2-yn-1-yl]benzyl]urea

The urea compound was prepared according to Example 22 using 3-chlorophenylacetylene instead of 2-chlorophenylacetylene.
Melting point: 118° to 119° C.
$^1$H-NMR: 4.54 (s, 2H); 5.59 (d, 6Hz, 1H); 6.18 (d, 6Hz, 1H); 6.36 (s, 2H); 7.31 (d, 8Hz, 2H); 7.36–7.50 (m, 6H); 9.36 (s, 1H)

EXAMPLE 24

N-Hydroxy-N-[4-[1-hydroxy-3-(4-chlorophenyl)prop-2-yn-1-yl]benzyl]urea

According to Example 22 the urea compound was prepared from 4-chlorophenylacetylene.
Melting point: 140° to 144° C.
$^1$H-NMR: 4.52 (s, 2H); 5.57 (d, 6Hz, 1H); 6.15 (d, 6Hz, 1H); 6.34 (s, 2H); 7.30 (d, 8Hz, 2H); 7.40–7.48 (m, 6H); 9.35 (s, 1H)

EXAMPLE 25

N-Hydroxy-N-[4-[1-hydroxy-3-(4-fluorophenyl)prop-2-yn-1-yl]benzyl]urea

According to Example 22 the urea compound was prepared from 4-fluorophenylacetylene.
Melting point: 136° C.
$^1$H-NMR: 4.53 (s, 2H); 5.57 (d, 6Hz, 1H); 6.14 (d, 6Hz, 1H); 6.37 (s, 2H); 7.21 (t, 9Hz, 2H); 7.30 (d, 8Hz, 2H); 7.47–7.53 (m, 4H); 9.36 (s, 1H)

The resulting racemic urea compound was separated into its enantiomers by chromatography with methanol/water 80:20 using tribenzoyl cellulose (10 to 20 μm; Riedl de Haen) as the stationary phase.

EXAMPLE 26

N-Hydroxy-N-[4-[1-hydroxy-3-(3-methoxyphenyl)-prop-2-yn-1-yl]benzyl]urea

The urea compound was prepared according to Example 22 using 3-methoxyphenylacetylene.
$^1$H-NMR: 3.66 (s, 3H); 4.47 (s, 2H); 5.42 (s, 2H); 5.55 (s, 1H); 6.79 (dd, 2Hz, 8Hz, 1H); 6.90 (m, 1H); 6.97 (d, 8Hz, 1H); 7.12 (t, 8Hz, 1H); 7.21 (d, 8Hz, 2H); 7.43 (d, 8Hz, 2H)

EXAMPLE 27

N-Hydroxy-N-[4-[1-hydroxy-3-(2-thienyl)prop-2-yn-1-yl]benzyl]urea

The urea compound was prepared according to Example 22 using 2-thienylacetylene.
$^1$H-NMR: 4.54 (s, 2H); 5.61 (d, 6Hz, 1H); 6.19 (d, 6Hz, 1H); 6.36 (s, 2H); 7.06 (dd, 2Hz, 5Hz, 1H); 7.29–7.32 (m, 3H); 7.46 (d, 8Hz, 2H); 7.56–7.58 (m, 1H); 9.37 (s, 1H)

EXAMPLE 28

N-Hydroxy-N-[4-[1-hydroxy-3-(3-thienyl)prop-2-yn-1-yl]benzyl]urea

The urea compound was prepared according to Example 22 using 3-thienylacetylene.
Melting point: 117° to 119° C.
$^1$H-NMR: 4.53 (s, 2H); 5.55 (d, 6Hz, 1H); 6.10 (d, 6Hz, 1H); 6.35 (s, 2H); 7.14–7.16 (m, 1H); 7.30 (d, 8Hz, 2H); 7.47 (d, 8Hz, 2H); 7.55–7.57 (m, 1H); 7.74–7.75 (m, 1H); 9.36 (s, 1H)

EXAMPLE 29

N-Hydroxy-N-[3-[1-hydroxy-3-phenyl-prop-2-yn-1-yl]benzyl]urea 1-(3-hydroxyareinomethylphenyl)-3-phenyl-prop-2-yn-1-ol was prepared according to Example 1 using isophthal aldehyde monodiethylacetal instead of terephthal aldehyde monodiethylacetal. Then the resulting hydroxylamine was converted in accordance with Example 8 into the respective urea compound melting at 144° to 146° C.
$^1$H-NMR: 4.56 (s, 2H); 5.59 (d, 6Hz, 1H); 6.16 (d, 6Hz, 1H); 6.35 (s, 2H); 7.23–7.49 (m, 9H); 9.38 (s, 1H)

EXAMPLE 30

N-Hydroxy-N-[3-[1-hydroxy-3-(3-thienyl)prop-2-yn-1-yl]benzyl]urea

The urea compound was prepared according to Example 29 using 3-thienylacetylene.
Melting point: 151° C.
$^1$H-NMR: 4.55 (s, 2H); 5.55 (d, 6Hz, 1H); 6.13 (d, 6Hz, 1H); 6.55 (s, 2H); 7.16 (dd, 1Hz, 5Hz, 1H); 7.22 (d, 8Hz, 1H); 7.32 (t, 8Hz, 1H); 7.41 (d, 8Hz, 1H); 7.46 (S, 1H); 7.66 (m, 1H); 7.76 (m, 1H); 9.37 (s, 1H)

EXAMPLE 31

N-Hydroxy-N-[3-[1-hydroxy-3-(3,4-dimethoxypheny)prop-2-yn-1-yl]benzyl]urea

The urea compound was prepared according to Example 29 using 3,4-dimethoxyphenylacetylene.
Melting point: 146° C.
$^1$H-NMR: 3.76 (s, 3H); 3.77 (s, 3H); 4.55 (s, 2H); 5.55 (d, 6Hz, 1H); 6.09 (d, 6Hz, 1H); 6.35 (s, 2H); 6.91–6.97 (m, 2H); 7.02 (dd, 2Hz, 8Hz, 1H); 7.23 (d, 8Hz, 1H); 7.33 (t, 8Hz, 1H); 7.42 (d, 8Hz, 1H); 7.47 (s, 1H); 9.38 (s, 1H)

EXAMPLE 32

N-Hydroxy-N-[1-[4-(1-hydroxy-3-phenyl-prop-2-yn-1-yl)phenyl]ethyl]urea

The hydroxylamine prepared according to Example 6 was converted into the corresponding diastereomeric urea following the procedure of Example 8.
$^1$H-NMR: 1.42 (d, 7Hz, 3H); 3.50 (s, 2H); 5.33 (q, 7Hz, 1H); 5.57 (s, 1H); 6.29 (s, 2H); 7.35–7.48 (m, 9H)

EXAMPLE 33

N-Hydroxy-N-[4-[1-ethoxy-3-(3,4-dimethoxyphenyl)prop-2-yn-1-yl]benzyl]acetamide

The acetamide compound was prepared according to Example 5 using 3,4-dimethoxyphenylacetylene.
$^1$H-NMR: 1.18 (t, 7Hz, 3H); 2.06 (s, 3H); 30 3.50–3.58 (m, 1H); 3.67–3.82 (m, 7H); 4.70 (s, 2H); 5.42 (s, 1H);

6.92 (d, 8Hz, 1H); 6.99 (d, 2Hz, 1H); 7.04 (dd, 8Hz, 2Hz, 1H); 7.31 (d, 8Hz, 2H); 7.50 (d, 8Hz, 2H); 9.89 (s, 1H)

EXAMPLE 34

N-Hydroxy-N-[4-[1-ethoxy-3-(3,4-dimethoxyphenyl)-prop-2-yn-1-yl]benzyl]urea

1-[4-hydroxyaminomethylphenyl]-3-[3,4-dimethoxyphenyl]1-ethoxy-prop-2-yne, prepared from 3,4-dimethoxyphenylacetylene according to Example 5, was converted into the corresponding urea compound following the procedure of Example 8.

$^1$H-NMR: 1.18 (t, 7Hz, 3H); 3.74–3.85 (m, 8H); 4.54 (s, 2H); 5.41 (s, 1H); 6.35 (s, 2H); 6.92 (d, 8Hz, 1H); 6.99 (d, 2Hz, 1H); 7.04 (dd, 2Hz, 8Hz, 1H); 7.32 (d, 8Hz, 2H); 7.47 (d, 8Hz, 2H); 9.34 (s, 1H)

EXAMPLE 35

N-Hydroxy-N-[4-[1-ethoxy-3-(2-thienyl)prop-2yn-1-yl]benzyl]urea

The urea compound was prepared according to Example 34 using 2-thienylacetylene.

$^1$H-NMR: 1.20 (t, 7Hz, 3H); 3.52–3.60 (m, 1H); 3.66–3.74 (m, 1H); 4.58 (s, 2H); 5.50 (s, 1H); 6.38 (s, 2H); 7.10 (dd, 2Hz, 5Hz, 1H); 7.37–7.40 (m, 3H); 7.48 (d, 8Hz, 2H); 7.63–7.65 (m, 1H); 9.39 (s, 1H)

EXAMPLE 36

N-Hydroxy-N-[4-[1-hydroxy-3-(3-pyridyl)prop-2yn-1-yl]benzyl]urea

The hydroxylamine prepared according to Example 1 using 3-pyridylacetylene was transformed into the corresponding urea compound following the procedure of Example 8.

Melting point: 145° C.

$^1$H-NMR: 4.53 (s, 2H); 5.62 (d, 5,8Hz, 1H); 6.21 (d, 5,9Hz, 1H); 6.35 (s, 2H); 7.29–7.55 (m, 5H); 7.84–7.87 (m, 1H); 8.53–8.55 (m, 1H); 8.62 (d, 1,6Hz, 1H); 9.36 (s, 1H)

EXAMPLE 37

N-Hydroxy-N-[3-[1-hydroxy-3-(3-pyridyl)prop-2-yn-1-yl]benzyl]urea

The urea compound was prepared according to Example 36 using isophthal aldehyde monodiethylacetal instead of terephthal aldehyde monodiethylacetal.

Melting point: 153° C.

$^1$H-NMR: 4.55 (s, 2H); 5.61 (d, 5,6Hz, 1H); 6.23 (d, 7,5Hz, 1H); 6.34 (s, 2H); 7.22–7.49 (m, 5H); 7.86 (d, 7,9Hz, 1H); 8.54 (d, 1,2Hz, 1H); 8.34 (s, 1H); 9.37 (s, 1H)

EXAMPLE 38

N-Hydroxy-N-[4-[1-hydroxy-3-(4-pyridyl)prop-2-yn-1-yl]benzyl]urea

The urea compound was prepared according to Example 36 using 4-pyridylacetylene.

$^1$H-NMR: 4.52 (s, 2H); 5.62 (d, 5,7Hz, 1H); 6.23 (d, 5,8Hz, 1H); 6.33 (s, 2H); 7.30 (d, 8,1Hz, 2H); 7.39 (d, 1,5Hz, 2H); 7.48 (d, 8,1Hz, 2H); 8.56 (d, 1,5Hz, 2H); 9.37 (s, 1H)

EXAMPLE 39

N-Hydroxy-N-[4-[1-hydroxy-2-(2-pyridyl)prop-2-yn-1-yl]benzyl]urea

The urea compound was prepared according to Example 36 using 2-pyridylacetylene.

Melting point: 140° to 142° C.

$^1$H-NMR: 4.52 (s, 2H); 5.61 (d, 5,8Hz, 1H); 6.23 (d, 5,9Hz, 1H); 6.34 (s, 2H); 7.29–7.38 (m, 3H); 7.47–7.51 (m, 3H); 7.76–7.81 (m, 1H); 8.54 (d, 4,8Hz, 1H); 9.34 (s, 1H)

EXAMPLE 40

N-Hydroxy-N-[3-[1-hydroxy-3-(2-pyridyl)prop-2-yn-1-yl]benzyl]urea

The urea compound was prepared according to Example 37 using 2-pyridylacetylene.

Melting (decomposition) Point:108° C.

$^1$H-NMR: 4.55 (s, 2H); 5.61 (d, 5,8Hz, 1H); 6.26 (d, 5,8Hz, 1H); 6.34 (s, 2H); 7.23–7.52 (m, 6H); 7.76–7.82 (m, 1H); 8.54 (d, 4,8Hz, 1H); 9.37 (s, 1H)

EXAMPLE 41

N-Hydroxy-N-[4-[1-hydroxy-3-(2-pyridyl)prop-2-yn-1-yl]benzyl]acetamide

The acetamide compound was prepared according to Example 1 using 2-pyridylacetylene.

$^1$H-NMR: 2.04 ( s, 3H); 4.68 ( s, 2H); 5.62 (d, 5,8Hz, 1H); 6.23 (d, 5,9Hz, 1H); 7.27–7.49 (m, 6H); 7.76–7.88 (m, 1H); 8.54 (d, 4,8Hz, 1H); 9.85 (s, 1H)

BIOLOGICAL INVESTIGATIONS

All stated IC$_{50}$-values are absolute values. Thin layer chromatography was carried out using silica gel Si 60 from E. Merck of Darmstadt, Germany as the stationary phase. "RP-HPLC" refers to reversed-phase high-pressure liquid chromatography. "HETE" refers to hydroxyeicosatetraenoic acid.

INHIBITION OF 5-LIPOXYGENASE 1. Inhibition of 5-lipoxygenase in RBL-1-cells

To determine the inhibition of 5-lipoxygenase, rat basophilic leukemia cells (RBL-1-cells) were cultured in vitro, harvested by centrifugation, washed with 50 mM potassium phosphate buffer of pH 7.4, and then suspended in this buffer at $1 \times 10^7$ cells/ml. Indomethacin (10 µM) and calcium chloride (2 mM) were added to 1 ml portions of this suspension, and then the mixture was incubated either in the presence of a compound according to the invention in a concentration range of from 0,1 µM to 100 µM or in the presence of a solvent (ethanol and/or dimethyl sulfoxide) for 3 minutes and thereafter with 20 µM of [$^{14}$C]-arachidonic acid and 20 µM of calcium ionophore A 23 187 for 10 minutes. The reaction was stopped by adding 20 µl of glacial acetic acid, and then the mixture was extracted with ethyl acetate to isolate the metabolites of arachidonic acid formed by the enzymatic action of 5-lipoxygenase. These were separated by thin layer chromatography using a solvent mixture known to be suitable for lipoxygenase products [c.f. Jakschik et al., *Biochem. Biophys. Res. Commun.* 102, 624 (1981)].

The distribution of radioactivity among the different metabolites of arachidonic acid was measured using a TLC Linear Analyzer. By correlating the percentage amounts of the products formed under the action of 5-lipoxygenase (5HETE, isomers of LTB$_4$) in the absence as well as in the presence of different concentrations of compounds according to the invention, the IC$_{50}$-values, i.e. the concentrations which cause a 50% inhibition of 5-lipoxygenase, were determined graphically from semilogarithmic plots. The results are summarized in the following table:

| Compound of Example No. | IC$_{50}$-Value [μM] |
| --- | --- |
| 1 | 5 |
| 2 | 4 |
| 3 | 5 |
| 4 | 4 |
| 5 | 4 |
| 8 | 7 |
| 9 | 4 |
| 10 | 4 |
| 11 | 8 |
| 13 | 3 |
| 15 | 3 |
| 16 | 3 |
| 17 | 5 |
| 19 | 5 |
| 22 | 4 |
| 23 | 4 |
| 24 | 3 |
| 25 | 3 |
| 26 | 4 |
| 27 | 3 |
| 28 | 4 |
| 29 | 4 |
| 33 | 5 |
| 35 | 3 |

2. Inhibition of Cell-free 5-lipoxygenase from RBL-1-cells

Cell-free 5-lipoxygenase was polarographically measured from 10,000 × g supernatant of homogenized rat basophilic leucemia cells (M. Haurand & L. Flohé in *Biol. Chem. HoppeSeyler* 369, 133 to 142 (1988)). After preincubation of the 10,000 × g supernatant with arachidonic acid (75 μM), ATP (adenosine triphosphate; 4 mM), reduced glutathione (4 mM), and either a compound according to the invention (0.1 to 100 μM) or a solvent (ethanol and/or dimethyl sulfoxide) at 35° C. for 5 minutes, the lipoxygenase reaction was initiated by addition of calcium chloride (3 mM) and simultaneously recorded.

The activity of 5-lipoxygenase was determined from the difference in the pO$_2$-decrease before and after addition of calcium chloride. The evaluation included the initial rate of the reaction after the lag-phase as well as the duration of the lag-phase. In the concentration range of from 3 to 50 μM, the test substances induced lag-phases between 20 and 60 seconds. The calculated IC$_{50}$-values are summarized in the following table:

| Compound of Example No. | IC$_{50}$-Value [μM] |
| --- | --- |
| 1 | 5 |
| 4 | 9 |
| 5 | 5 |
| 6 | 8 |
| 8 | 8 |
| 13 | 3 |
| 15 | 7 |
| 16 | 6 |
| 20 | 7 |
| 22 | 8 |
| 25 | 3 |
| 33 | 6 |
| 35 | 5 |

3. Inhibition of Leukotriene-synthesis Induced by FMLP/merthiolate of Human Polymorphonuclear Leukocytes Human granulocytes were isolated by dextran sedimentation and a Percoll gradient method and suspended in HBSS (Hanks buffered saline solution) at 1×10$^7$ cells/ml. The cells were incubated in the presence of a compound according to the invention or a solvent (ethanol and/or dimethyl sulfoxide) at 37° C. for 2 minutes, then with merthiolate (sodium ethylmercurithiosalicylate; 40 μM) for 2 minutes and thereafter with FMLP (formyl-methionyl-leucylphenylalanine; 10$^{-7}$M) for 15 minutes. After solid phase extraction, the metabolites of arachidonic acid 5-HETE, LTB$_4$, 6-trans-LTB$_4$-isomers, 20-OH-LTB$_4$ and 20-COOH-LTB$_4$ were identified by RP-HPLC (M. Haurand and L. Flohé in *Biochem. Pharmacol.* 38, 2129 to 2137 (1989)).

To investigate the reversibility of the inhibitory action, the cells were incubated with a compound according to the invention or a solvent (ethanol and/or dimethyl sulfoxide) at 37° C. for 5 minutes, centrifuged at 300 × g for 5 minutes, and resuspended in 2 ml of HBSS. Then the cells were incubated with merthiolate (40 μM) at 37° C. for 2 minutes and thereafter with FMLP (10$^{-7}$M) for 15 minutes. The IC$_{50}$-value of the reversible inhibitory action was 2 μmolar when the compound prepared according to Example 1 was used.

4. Inhibition of 5-lipoxygenase in Rat Blood After Oral Administration.

The bioavailability of the compounds of formula I as 5-lipoxygenase inhibitors was characterized by means of an ex vivo biochemical assay method described by Tateson et al. in *Brit. J. Pharmacol.* 94, 528 (1988): A compound of formula I was orally administered to male rats (Wistar strain) at a dose of 21.5 mg/kg. After lethal CO$_2$-narcosis one hour after administration, the rats were bled by heart puncture with added heparin as an anticoagulant. Aliquots of the whole blood were incubated at 37° C. for 30 minutes in a water bath with calcium ionophore A 23 187 at an end concentration of 15 μg/ml. At the end of the incubation, the samples were centrifuged, and the concentration of the immunoreactive LTB$_4$(iLTB$_4$) in aliquots of cell-free plasma was determined by radioimmunoassay (3H-LTB$_4$-RIA, Amersham). To enable calculation of the inhibition in percent of ex vivo iLTB$_4$-formation in whole rat blood treated with a compound according to the invention, rats orally treated with an appropriate vehicle solution were included in all experiments, and aliquots of their blood were run in parallel and were processed in the same way as described. The average iLTB$_4$-content of the plasma of the vehicletreated rats served as a 100% value. The activity in percent of the ex vivo iLTB$_4$-formation after oral administration of a compound according to the invention was calculated by dividing the average value of the iLTB$_4$-contents in ng iLTB$_4$/ml of the group treated with a compound according to the invention by the average value of the iLTB$_4$-contents in ng iLTB$_4$/ml of the vehicle treated group and subsequent multiplication by a factor of 100. The respective inhibition in percent was calculated by subtracting the activity in percent from 100. The following table shows the resulting inhibition values after oral administration of 21.5 mg/kg of compounds according to the invention:

| Compound of Example No. | Inhibition [%] |
| --- | --- |
| 1 | 93 |
| 8 | 65 |
| 10 | 75 |
| 11 | 95 (dose 10 mg/kg) |
| 15 | 71 |

-continued

| Compound of Example No. | Inhibition [%] |
| --- | --- |
| 17 | 77 |
| 22 | 83 (dose 10 mg/kg) |

INHIBITION OF 12-LIPOXYGENASE

1. Inhibition of 12-HETE- and 5S,12S-DiHETE-synthesis induced by FMLP/merthiolate of human polymorphonuclear leukocytes and thrombocytes Coincubations of human granulocytes and thrombocytes were carried out and investigated for inhibition of leukotriene-synthesis induced by FMLP/merthiolate. 12-HETE and 5S, 12S-DiHETE were additionally included into the evaluation. The $IC_{50}$-value of the inhibitory action on 12-lipoxygenase was 5 µmolar when the compound prepared according to Example 1 was used.

2. Inhibition of 12-lipoxygenase in homogenates of human thrombocytes.

Human thrombocytes were suspended at $3 \times 10^9$ cells/ml, fumigated with nitrogen, and sonicated with ultrasonic energy while cooling in ice water. After centrifugation at 10.000 × g for 15 minutes, reduced glutathione (3 mM) was added. 1 ml portions of the 10,000 × g supernatant were incubated with a compound according to the invention or with ethanol at 25° C. for 4 minutes and then with 1-$^{14}$C-labelled arachidonic acid (40 µM) for 7.5 minutes. In addition, indomethacin (10 µM) was added to each sample. The reaction was stopped by adding acetic acid, and then the metabolites of arachidonic acid were extracted with ethyl acetate and analyzed by thin layer chromatography. The distribution of the $^4$C-labelled fractions was measured using a TLC-linear analyzer. The $IC_{50}$-values were determined graphically from semilogarithmic plots. The $IC_{50}$-value of the inhibitory action on 12-Lipoxygenase was 1 µmolar when the compound prepared according to Example 1 was used.

3. Inhibition of 12-lipoxygenase in human blood 3 ml aliquots of human whole blood treated with heparin were incubated either with a compound according to the invention or with dimethyl sulfoxide at 37° C. for 5 minutes. Then 12-lipoxygenase was activated by addition of calcium ionophore A 23 187 (15 µg/ml blood). After incubation at 37° C. for 30 minutes and centrifugation, cell-free plasma was obtained. Plasma protein was precipitated by addition of 2 ml of ethanol per ml of plasma and then separated by centrifugation. After adjusting the ethanol content in the supernatant with water to 10% by volume, the 12-lipoxygenase product 12-HETE was enriched by solid phase extraction using an octadecyl silica column. The methanolic eluate was evaporated to dryness, diluted in 40% by volume of methanol, and the 12-HETE-content was determined by HPLC. The $IC_{50}$-values of the compounds of the invention prepared according to Examples 1, 8 and 16 were 2, 4 and 3 µmolar, respectively.

INHIBITION OF CYCLOOXYGENASE

Sheep seminal vesicle microsomes (80 µg protein/ml buffer; 50 mM potassium phosphate buffer of pH 7.4) in 1 ml aliquots were incubated with arachidonic acid (20 µM; 150,000 dpm; 1-$^{14}$C) and either with a compound according to the invention (0.1 to 100 µM) or with a solvent (ethanol and/or dimethyl sulfoxide) at 20° C. for 15 minutes. After addition of acetic acid and extraction with ethyl acetate, the metabolites of arachidonic acid were separated by thin layer chromatography into a fraction containing prostaglandins and a fraction containing arachidonic acid. The distribution of the different $^{14}$C-labelled fractions was measured using a TLC linear analyzer. By correlating the percentages of the amounts of the product formed under the action of cyclooxygenase in the presence of solvent and in the presence of different concentrations of compounds according to the invention, the $IC_{50}$-values of the compounds prepared according to Examples 1, 4, 8, 18, 20, 22, 23, 25 (racemic compound as well as enantiomers), 26, 28 to 31 and 35 were all >500 µM, thereby indicating that none of the tested substances had an inhibiting effect on cyclooxygenase.

ALLERGEN-INDUCED BRONCHOCONSTRICTION IN GUINEA PIGS
(Konzett-Rössler)

The anti-asthmatic effect of compounds according to the invention was tested in anesthetized and ventilated guinea pigs. To induce an asthmatic reaction, the animals were passively sensitized by a single intraperitoneal injection of anti-ovalbumin serum. After 48 hours, the asthmatic reaction was elicited by intravenous challenge with 0.2 mg/kg of ovalbumin. The immediately resulting bronchoconstriction was measured as an increase in intratracheal pressure. Effects caused by histamine, serotonin and sympathic counterreaction were eliminated by intravenous pretreatment with 2.15 mg/kg of mepyramine, 46.4 µg/kg of propranolol, 4.64 mg/kg of atropine and 1 mg/kg of methysergide, all administered 5 minutes before challenge. Compounds according to the invention were administered orally 60 minutes before the administration of ovalbumin. The following $ED_4$-values for the inhibition of the bronchoconstriction elicited by ovalbumin, i.e. the effective doses causing a 40% average inhibition of the bronchoconstriction, were determined:

| Compound of Example No. | $ED_{40}$-Value [mg/kg] |
| --- | --- |
| 1 | 17 |
| 3 | 9 |
| 23 | 18 |
| 25 | 10 |
| 26 | 17 |
| 28 | 17 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. An oxyalkyne compound corresponding to the formula I

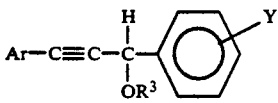

wherein
the substituent Y in the meta- or para-position is

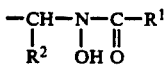

$R^1$ represents $CH_3$ or $NH_2$;
$R^2$ represents H or $CH_3$;
$R^3$ represents H, $C_{1-3}$-alkyl or $COCH_3$, and
Ar represents an aromatic residue selected from the group consisting of

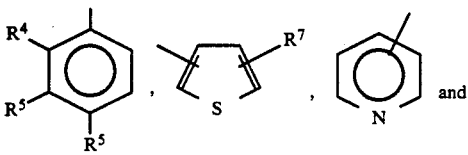

wherein
$R^4$, $R^5$ and $R^6$ are each independently selected from the group consisting of H, F, Cl, Br, $C_{1-6}$-alkyl, $CF_3$ and $C_{1-6}$-alkoxy, and
$R^7$ represents H, F, Cl, Br, $C_{1-3}$-alkyl or $CF_3$ in the form of racemates or mixtures of diastereoisomers or in optically active form.

2. An oxyalkyne compound according to claim 1, wherein $R^2$ is H.

3. An oxyalkyne compound according to claim 1 wherein $R^3$ is H.

4. An oxyalkyne compound according to claim 1, wherein $R^4$, $R^5$ and $R^6$ are each independently selected from the group consisting of H, F, Cl and $OCH_3$.

5. An oxyalkyne compound according to claim 1, wherein at least one of $R^4$, $R^5$ and $R^6$ is H.

6. An oxyalkyne compound according to claim 1, wherein Ar is phenyl or 4-fluorophenyl.

7. An oxyalkyne compound according to claim 1, wherein $R^7$ is H.

8. An oxyalkyne compound according to claim 1, wherein $R^1$ is $CH_3$.

9. An oxyalkyne compound according to claim 1, wherein $R^1$ is $NH_2$.

10. A pharmaceutical composition comprising from 0.01 to 1000 mg per unit dose of at least one oxyalkyne compound according to claim 1, and a pharmaceutically acceptable carrier, diluent or solvent.

11. A pharmaceutical composition according to claim 10, in orally administrable form comprising from 1 to 1000 mg per unit dose of said at least one oxyalkyne compound.

12. A process for preparing a pharmaceutical composition according to claim 10, comprising admixing said at least one oxyalkyne compound with a pharmaceutically acceptable carrier, diluent or solvent, and forming the resulting admixture into unit doses each containing from 0.01 to 1000 mg of said at least one oxyalkyne compound.

13. A process according to claim 12, further comprising incorporating in said composition at least one adjuvant selected from the group consisting of pharmaceutically acceptable binders, tablet disintegrating agents.

14. A process according to claim 12, wherein the resulting admixture is formed into a dosage form selected from the group consisting of tablets, dragees, capsules, granules, drops, syrups, suppositories, plasters, solutions, suspensions, reconstitutible dry formulations, and sprays.

15. A process for preparing an oxyalkyne compound corresponding to the formula I

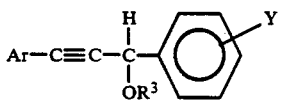

wherein
the substituent Y in the meta- or para-position is

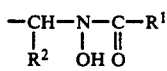

$R^1$ represents $CH_3$ or $NH_2$;
$R^2$ represents H or $CH_3$;
$R^3$ represents H, $C_{1-3}$-alkyl or $COCH_3$;
Ar represents an aromatic residue selected from the group consisting of

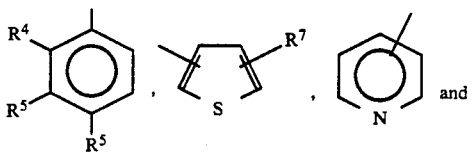

wherein
$R^4$, $R^5$ and $R^6$ are each independently selected from the group consisting of H, F, Cl, Br, $C_{1-6}$-alkyl, $CF_3$ or $C_{1-6}$-alkoxy, and
$R^7$ is H, F, Cl, Br, $C_{1-3}$-alkyl or $CF_3$;
said process comprising
reacting an alkyne corresponding to the formula II

with a partially protected terephthal or isophthal aldehyde corresponding to the formula III

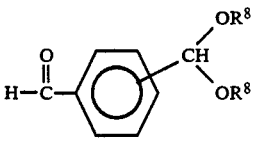

wherein $R^8$ represents $CH_3$ or $CH2CH3$, or both $R^8$ residues together represent the ethylene group, in the presence of a base to form an acetal corresponding to the formula IV

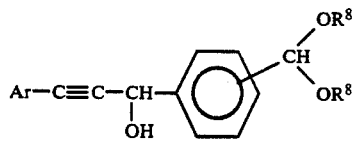

reacting the resulting acetal with an acid in a water containing solvent to form a hydroxyaldehyde corresponding to the formula V

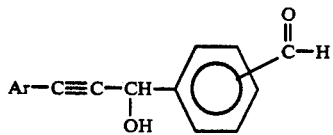

converting the resulting hydroxyaldehyde into an oxime corresponding to the formula VI

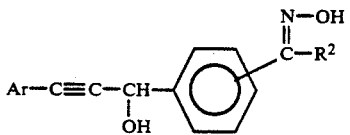

by either
reacting a hydroxy aldehyde of formula V with hydroxyl amine or a salt thereof in the presence of a base, or
substituting the alcoholic proton of the hydroxy aldehyde of formula V with an acid cleavable group which does not react with a Grignard reagent, then reacting the substituted compound of formula V with a methyl magnesium halogenide in an anhydrous nucleophilic solvent to form a secondary alcohol; oxidizing the resulting secondary alcohol with an oxidizing agent to form a keto compound; and splitting off the acid cleavable group from the resulting keto compound with an acid to form into a keto compound corresponding to the formula Va

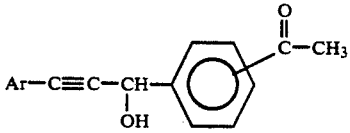

reacting the resulting keto compound of formula Va with a hydroxylamine or a salt thereof in the presence of a base to form an oxime corresponding to the formula VI

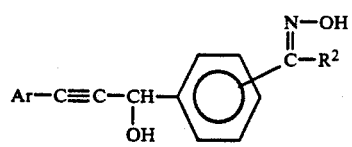

reducing the resulting oxime with a boron-containing reducing agent in the presence of an acid, and optionally a $C_{1-3}$-alcohol, to form a hydroxylamine corresponding to the formula VII

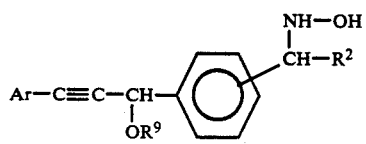

wherein $R^9$ represents H or $C_{1-3}$-alkyl, and
converting the resulting hydroxylamine of formula VII into an oxyalkyne compound of formula I by
a) reacting the hydroxylamine of formula VII with trimethylsilyl isocyanate or an alkali cyanate, and hydrolyzing the resulting product, or With phosgene and subjecting the resulting product to aminolysis, or
b) reacting the hydroxylamine of formula VII with an acetylating agent to form a bis-acetyl compound, and treating the resulting acetylated product with a base to split off the O-acetyl group, and optionally converting the propargylic $OCOCH_3$-group into an OH—group.

16. A process according to claim 15, wherein a hydroxy aldehyde of formula V is converted to an oxime.

17. A process according to claim 15, wherein an oxime is reduced in absence of a $C_{1-3}$-alkyl alcohol.

18. A process according to claim 15, wherein an oxyalkyne compound of formula I is prepared in which $R^3$ is H.

19. A method of treating a patient suffering from a disorder attributable to the action of leukotrienes, said method comprising administering to said patient an effective 5-lipoxygenase inhibiting amount of at least one oxyalkyne compound according to claim 1.

20. A method of treating a patient suffering from asthma, said method comprising administering to said patient an effective asthma symptom-relieving amount of at least one oxyalkyne compound according to claim 1.

* * * * *